(12) United States Patent
Kienzle, III et al.

(10) Patent No.: US 6,887,245 B2
(45) Date of Patent: May 3, 2005

(54) SURGICAL DRILL FOR USE WITH A COMPUTER ASSISTED SURGERY SYSTEM

(75) Inventors: Thomas C. Kienzle, III, Lake Forest, IL (US); Jon T. Lea, Lake Bluff, IL (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 129 days.

(21) Appl. No.: 10/186,010

(22) Filed: Jun. 27, 2002

(65) Prior Publication Data

US 2002/0193800 A1 Dec. 19, 2002

Related U.S. Application Data

(62) Division of application No. 09/878,588, filed on Jun. 11, 2001, now Pat. No. 6,478,802.

(51) Int. Cl.$^7$ .................................................. A61B 17/00
(52) U.S. Cl. ....................................................... 606/80
(58) Field of Search ............................. 606/80, 96, 130, 606/172; 408/225, 13, 15, 16, 97; 600/407, 434, 427, 414, 417, 411

(56) References Cited

U.S. PATENT DOCUMENTS

| | | | |
|---|---|---|---|
| 5,251,127 A | 10/1993 | Raab | |
| 5,383,454 A | 1/1995 | Bucholz | |
| 5,445,166 A | 8/1995 | Taylor | |
| 5,517,990 A | 5/1996 | Kalfas | |
| 5,584,838 A * | 12/1996 | Rona et al. | 606/96 |
| 5,622,170 A | 4/1997 | Schulz | |
| 5,638,819 A | 6/1997 | Manwaring | |
| 5,772,594 A | 6/1998 | Barrick | |
| 5,776,064 A | 7/1998 | Kalfas et al. | |
| 5,834,759 A * | 11/1998 | Glossop | 250/203.1 |
| 5,841,830 A | 11/1998 | Barni | |
| 5,904,691 A * | 5/1999 | Barnett et al. | 606/130 |
| 5,921,992 A * | 7/1999 | Costales et al. | 606/130 |
| 5,987,960 A * | 11/1999 | Messner et al. | 73/1.79 |
| 6,006,127 A | 12/1999 | Van Der Brug | |
| 6,021,343 A | 2/2000 | Foley | |
| 6,064,904 A | 5/2000 | Yanof | |
| 6,081,741 A * | 6/2000 | Hollis | 600/424 |
| 6,226,548 B1 | 5/2001 | Foley et al. | |
| 6,235,038 B1 * | 5/2001 | Hunter et al. | 606/130 |
| 6,236,875 B1 * | 5/2001 | Bucholz et al. | 600/407 |
| 6,285,902 B1 | 9/2001 | Kienzle, III et al. | |
| 6,317,616 B1 * | 11/2001 | Glossop | 600/407 |
| 6,478,802 B2 * | 11/2002 | Kienzle et al. | 606/130 |

OTHER PUBLICATIONS

Lavalee, et al, "Computer Assisted Spine Surgery: a technique for accurate transpedicular screw fixation using CT data and a 3–D optical localizer", published in Proceedings of the First International Symposium on Medical Robotics and Computer Assisted Surgery, Pittsburg, PA, Sep. 22–24, 1994.

Carrat, et al, "Treatment of Pelvic Ring Fractures: Percutaneous Computer Assisted IIiosacral Screwing," published in MICCAI, 1998.

Carrat, et al, "Percutaneous Computer Assisted Iliosacral Screwing: Clinical Validation," published in MICCAI, 2000.

* cited by examiner

*Primary Examiner*—Pedro Philogene
(74) *Attorney, Agent, or Firm*—McAndrews, Held & Malloy, Ltd.; Peter J. Vogel; Michael A. Dellapenna

(57) ABSTRACT

A surgical drill for use with a computer assisted surgery system. In a first embodiment, at least three localizing emitters are mounted on and integral with each side of the drill housing, the emitters on each side arranged such that they are visible to a localizing device when that side is facing the localizing device. The emitters on each side are spaced sufficiently apart from one another to provide accurate pose information. In a second embodiment, the emitters are mounted on both sides of a two-sided fin assembly attached to the housing.

3 Claims, 8 Drawing Sheets

SURGICAL DRILL FOR USE WITH A COMPUTER ASSISTED SURGERY SYSTEM

REFERENCE TO PRIOR APPLICATION

This is a divisional of application Ser. No. 09/878,588, filed Jun. 11, 2001, now U.S. Pat. No. 6,478,802.

BACKGROUND OF THE INVENTION

1. Field of the Invention

This invention relates to a surgical drill for use with a computer assisted surgery system.

2. Description of the Related Art

Computer assisted surgery systems have been developed to aid a surgeon in more accurately positioning instruments during a surgical procedure. These systems have been described for use with CT images, fluoroscopic images, and images derived from other modalities as well as without images or in conjunction with a surgical robot. When using images of a patient, they are often referred to as image guided surgery systems. These systems typically use a localizing device to track surgical instruments in real time. One commonly used localizing device is an optical localizer that employs a stereoscopic camera system to view infrared light emitters or reflectors that are placed on the surgical instruments. Other localizing devices may use electromagnetic radiation or a passive manipulator arm with position encoders at the joints. The computer assisted surgery system then uses the information regarding the instrument's position to superimpose a representation of the instrument over the images or to generate some other graphic or alphanumeric display.

Commonly, surgical procedures performed with computer assisted surgery systems involve the insertion into the patient of an elongate instrument such as a drill bit or a probe. In these cases the computer-assistance may consist of superimposing a line representing the trajectory of the drill or probe over images of the patient. Many systems additionally provide for a means for determining the location of the tip of the probe or drill bit. By comparing this tip location to the location of a target feature in the body, the software can calculate the distance remaining in the trajectory. This information can be displayed as a bar graph as taught by U.S. Pat. Nos. 5,251,127 and 6,006,127 or as a numeric value or other graphic as taught by U.S. Pat. No. 5,638,819. However, these approaches are not suitable for orthopaedic procedures, where the surgeon does not typically record a target point prior to the procedure.

Another problem with the approach of tracking the drill itself is that the drill bit may bend. This can cause the trajectory displayed by the computer assisted surgery system to be significantly different than the actual path of the drill bit. Bending of the drill bit is most likely to occur at a location between the drill and the body part, either as a result of deflection of the drill bit tip upon entering the body part or because of lateral forces placed on the drill by the surgeon. One way to alleviate this problem is to use a tool guide that allows the trajectory of the drill bit or probe to be measured as it enters the body part. Such tool guides are common in orthopaedic surgery and neurosurgery.

Computer assisted versions of tool guides are described in U.S. Pat. Nos. 5,517,900 and 5,904,691, among others. With a tool guide placed flush against the bone the opportunity for drill bit bending is minimized and the trajectory displayed by the computer more closely matches the actual trajectory. However, tracking just the tool guide provides information regarding only the trajectory of the drill bit and not its progress into the body.

The present invention provides the surgeon with improved information for more accurately inserting a drill bit or other elongate object into the body, when used with a drill guide and a computer assisted surgery system.

SUMMARY OF THE INVENTION

Accordingly, one objective of the present invention is to provide a computer assisted surgery system for accurately positioning a drill bit into a body part.

Another objective of the invention is to provide a technique and apparatus for calculating and graphically displaying the pose of a drill bit attached to a drill and passed through a drill guide by determining the poses of the drill and drill guide. The invention has the advantage of accurately displaying the orientation and location of the drill bit.

Still another objective of the invention is to provide a technique and apparatus for reporting to the surgeon misalignment, malposition, or excessive bending of the drill bit relative to the drill guide.

Yet another objective of the invention is to provide a technique and apparatus for accurately calculating and graphically displaying the pose of a drill bit attached to a drill with only a single visible localizing emitter and passed through a drill guide.

Still another object of the invention is to provide a surgical drill, with three or more localizing emitters integrated into the drill housing, whose pose can readily be determined with the use of a localizer.

These and other objects of the present invention are achieved by the use of a computer assisted surgery system, including a drill and a drill guide, each outfitted with three or more localizing emitters, and an optical localizer for measuring the pose of the drill and drill guide. A drill bit is attached to the drill and the location of the tip of the drill determined during a calibration step in which the tip of the drill is placed against a dimple in the drill guide and the poses of the two instruments recorded. During drilling, the drill bit is inserted through the bore of the drill guide and the poses of the drill guide and drill are recorded in real time. The pose of the drill bit is calculated from the orientation of the drill guide and the location of the drill. A graphic representation of the drill bit is then displayed on the monitor screen in an appropriate position relative to the stored images or other instruments.

In an alternative embodiment of the drill, the three or more localizing emitters are integrated into the drill housing and are spaced widely apart to facilitate accurate pose determination.

In an alternative embodiment of the computer assisted surgery system, the drill may be outfitted with one or more localizing emitters. In the calibration step, the distance between the drill's localizing emitter and the tip of the drill is determined. During drilling, the pose of the drill bit is calculated from the orientation of the drill guide and the location of the drill's localizing emitters, prior to display of its representation on the monitor screen.

DETAILED DESCRIPTION OF THE INVENTION

The present invention is preferably operated in conjunction with an image guided surgery system such as is disclosed in U.S. patent application Ser. No. 09/248,133 entitled "Computer Assisted Targeting Device for Use in Orthopaedic Surgery". In the preferred embodiment, this image guided system comprises a computer, a display monitor, an optical localizing device, and surgical instruments outfitted with infrared LEDs as localizing emitters viewable by the optical localizer. During surgery the system functions by acquiring x-ray images with a C-arm fluoroscope of the involved body part. An optical localizer is capable of measuring the location of surgical instruments outfitted with a single emitter and the pose (location and orientation) of surgical instruments with three or more emitters. The system then superimposes on the images graphic representations of the instruments at their current positions. This allows the surgeon to view, in real time, the position of the instruments with respect to an imaged body part or with respect to other instruments.

Figure 1:
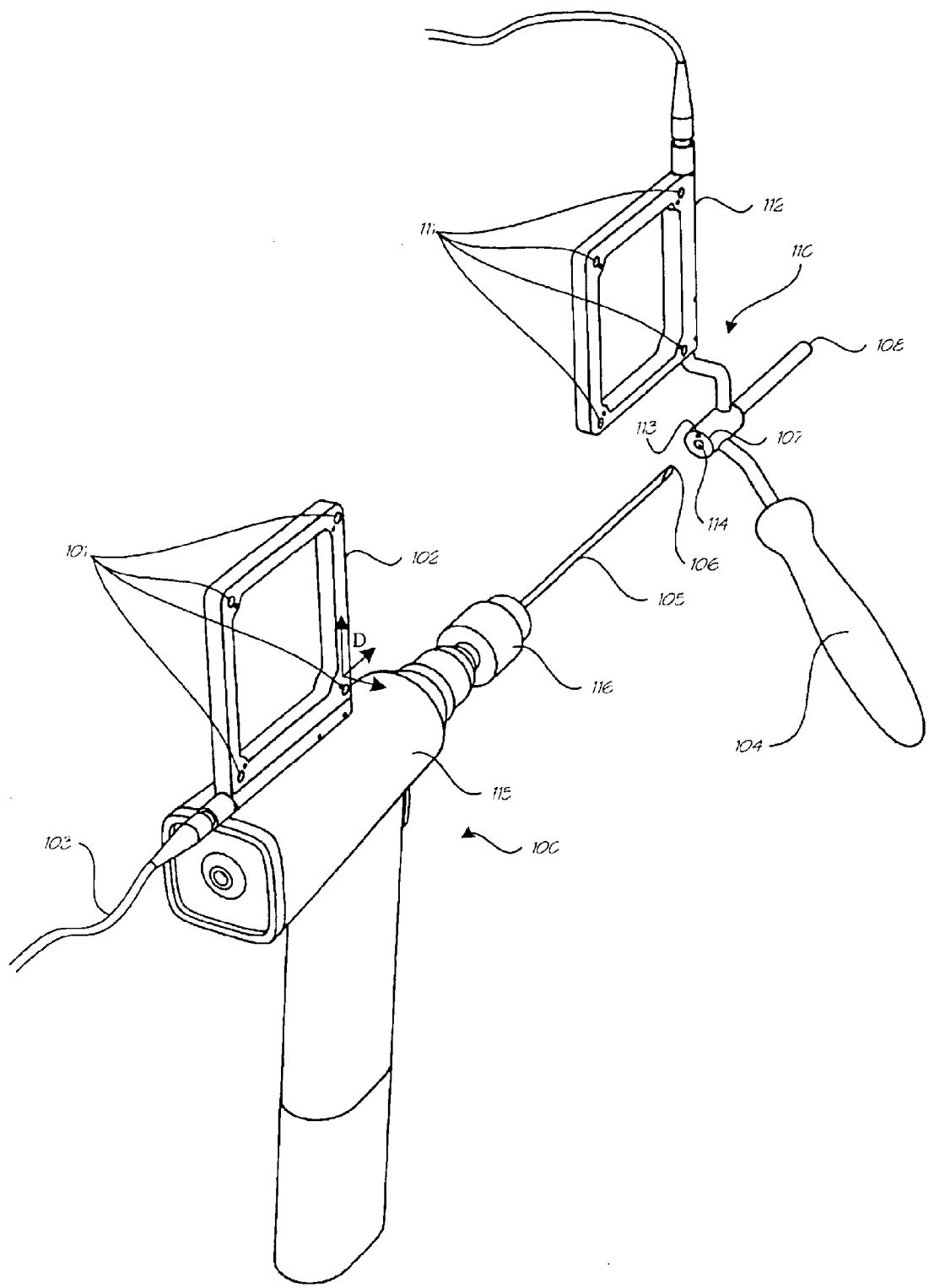
FIG. 1 is a perspective view of a drill and drill guide with attached housings containing localizer emitters according to the present invention.

In the preferred embodiment of the present invention, the surgical instruments are a drill guide and a drill with an attached drill bit. As shown in FIG. 1, the drill guide 110 comprises a bore or channel portion 114 through which may pass the drill bit 105. The bore portion 114 has a proximal end (drill bit entrance) 107 and a distal end (drill bit exit) 108. The bore portion of the drill guide functions to direct the drill bit, which passes through it on a trajectory that matches that of the bore. The drill guide 110 further comprises a fin assembly 112 that houses eight localizing emitters 111, four on either face of the fin assembly 112, in known locations relative to the bore portion 114. In an alternative embodiment, fewer localizing emitters may be used as long as there are at least three emitters visible to the localizing device during use. The localizing emitters may comprise reflectors, spheres, visible spectrum emitters, or any other suitable devices capable of being accurately located by an optical localizer. Alternatively, other localizing devices may be employed including acoustic localizers, electromagnetic localizers, or passive manipulators. Optionally, a handle 104 may be attached to the drill guide 110 to provide a convenient means for its manual positioning.

The drill guide 110 preferably also comprises a calibration portion, such as a dimple 113 or other indentation on a surface of the drill guide 110 capable of accepting a tip 106 of a drill bit 105 or other elongate object in a repeatable and accurate manner. The dimple 113 is located in a known relationship to the localizing emitters 111. Any other feature of the drill guide 110 capable of constraining the tip of an elongate object in a known location relative to the drill guide's localizing emitters 101 may be used without departing from the present invention.

In the preferred embodiment of the present invention, the drill 100 comprises a drill housing 115 and a rotating chuck 116 capable of firmly gripping a drill bit 105. The drill 100 has an axis of rotation about which the chuck 116 rotates relative to the drill housing 115. For calculation purposes, a reference frame may be assigned with one axis coincident with the axis of rotation and the origin assigned at the point of attachment of the drill bit to the drill. The drill 100 further comprises an attached fin assembly 102 that houses eight localizing emitters 101, four on either face, in known locations relative to the drill's axis of rotation, such that they define a drill emitter coordinate frame, D.

Figure 2:
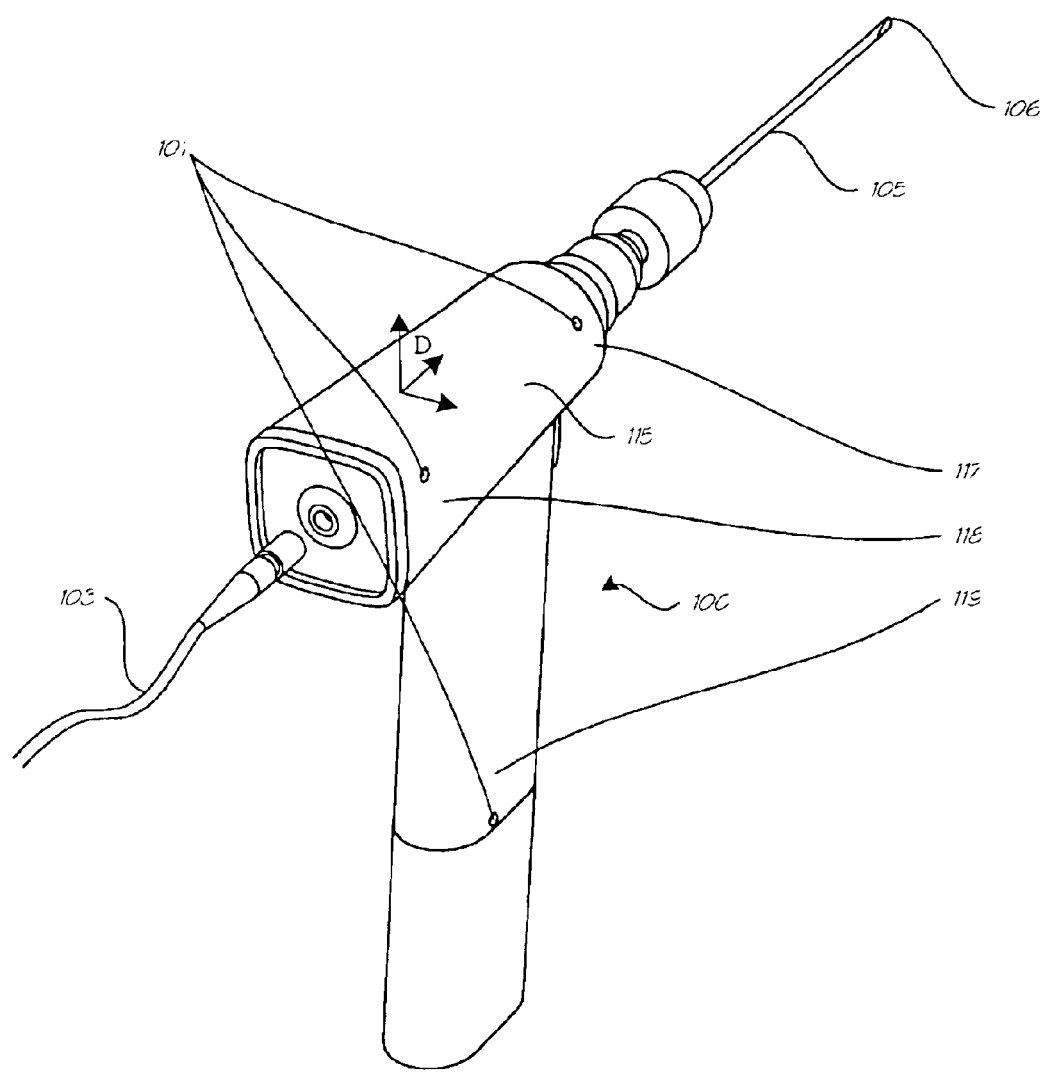
FIG. 2 is a perspective view of a drill with localizer emitters integrated into the drill housing.

In an alternative embodiment shown in FIG. 2, the drill 100 comprises six localizing emitters 101, three localizing emitters 101 on each side of the drill housing 115, which are arranged in a novel and characteristic manner and which define a drill emitter coordinate frame, D. A novel aspect of this invention is that the emitters 101 on the drill 100 are integral to the standard drill housing 115 and that the requisite wide spacing of the emitters 101 is achieved by placing them at the ends of the drill body 117, 118 and the bottom area of the handle 119, areas which are readily visible to the localizing device and are not likely to be obstructed by the surgeon's hand. Further, the spacing of the emitters 101 is wider than would be achieved by a typically dimensioned fin 102, and thus greater pose accuracy is possible. Alternatively, any arrangement of emitters that allows the localizer to determine the pose of the drill emitter coordinate frame with sufficient accuracy may be used without departing from the instant invention.

The emitters 101 are activated by signals supplied by a cable 103 from the optical localizer. This cable 103 may share functions with a power supply or other cable. Alternatively, the emitters 101 may be activated by a cableless system in which the power is supplied by a battery in the drill 100 or a separate battery. In an alternative embodiment, the localizing emitters may comprise reflectors, spheres, visible spectrum emitters, or any other suitable devices capable of being identified and accurately localized by an optical localizer. Alternatively, other localizing devices may be employed including acoustic localizers, electromagnetic localizers, or passive manipulators.

In the preferred embodiment, the computer assisted surgical system displays graphic representations of surgical instruments by measuring the pose of the instrument and then simulating the projection of points of a 3-D model of the instrument at its measured pose onto a 2-D plane associated with the C-arm at the time the x-ray images are acquired. For the drill guide, the 3-D model is preferably a vertex and line representation of a tube defining the portion of the drill guide containing the bore and a trajectory line representing an extension of the bore of the drill guide. For the drill, the 3-D model is a vertex and line representation of the drill bit that is inserted into the drill's chuck. Alternatively, the graphic representation of an instrument may be any model that includes information about its functional features from a complex surface or solid rendering of the entire instrument to a simple line trajectory for the drill guide or an "X" to represent the tip of the drill bit. In an alternative embodiment, these models may be projected onto any arbitrarily defined 2-D plane to display one instruments relative to another instrument.

Figure 3:
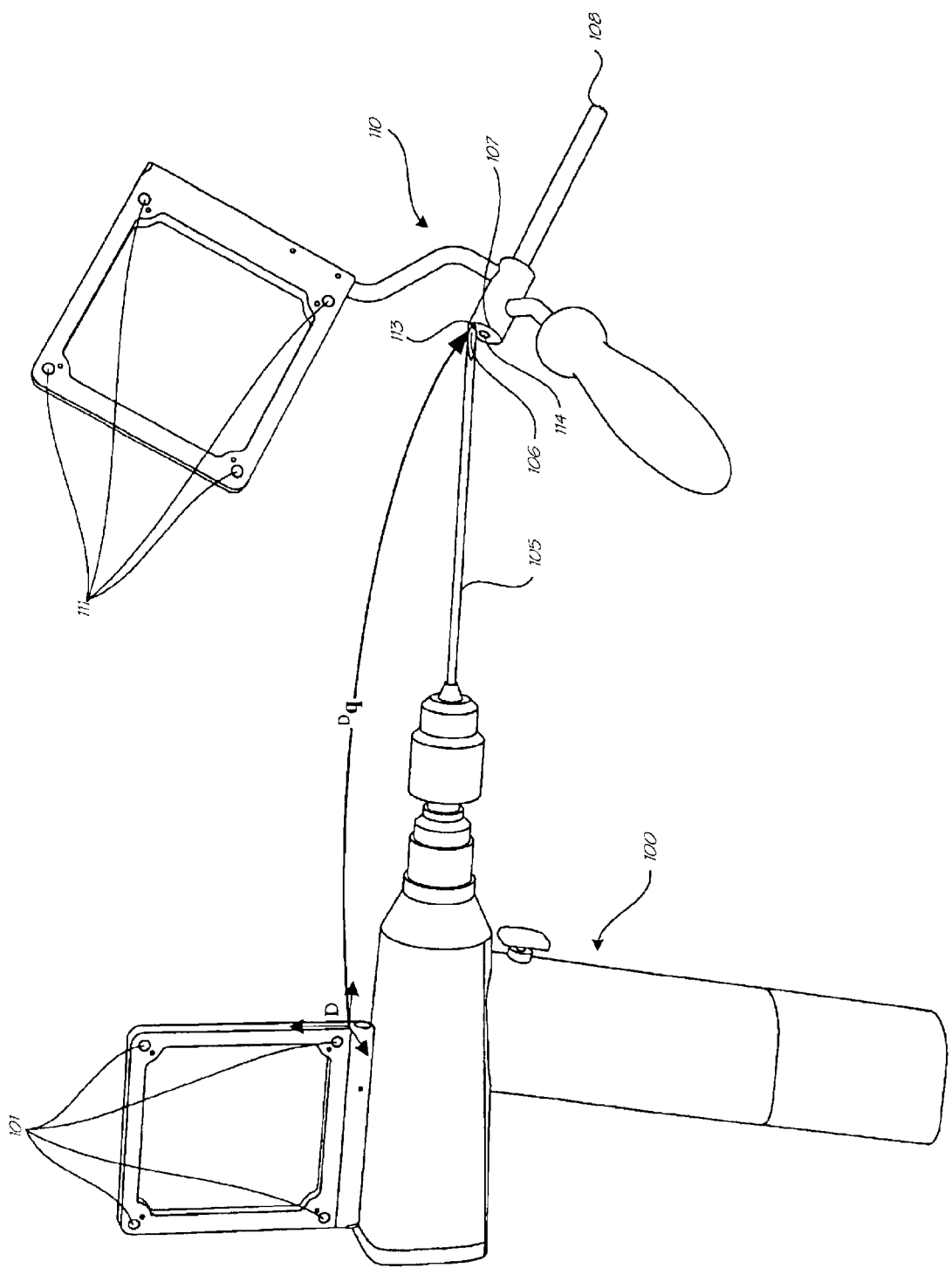
FIG. 3 is a perspective view of the drill of FIG. 1 and a drill guide in position for calibration.
Figure 4:
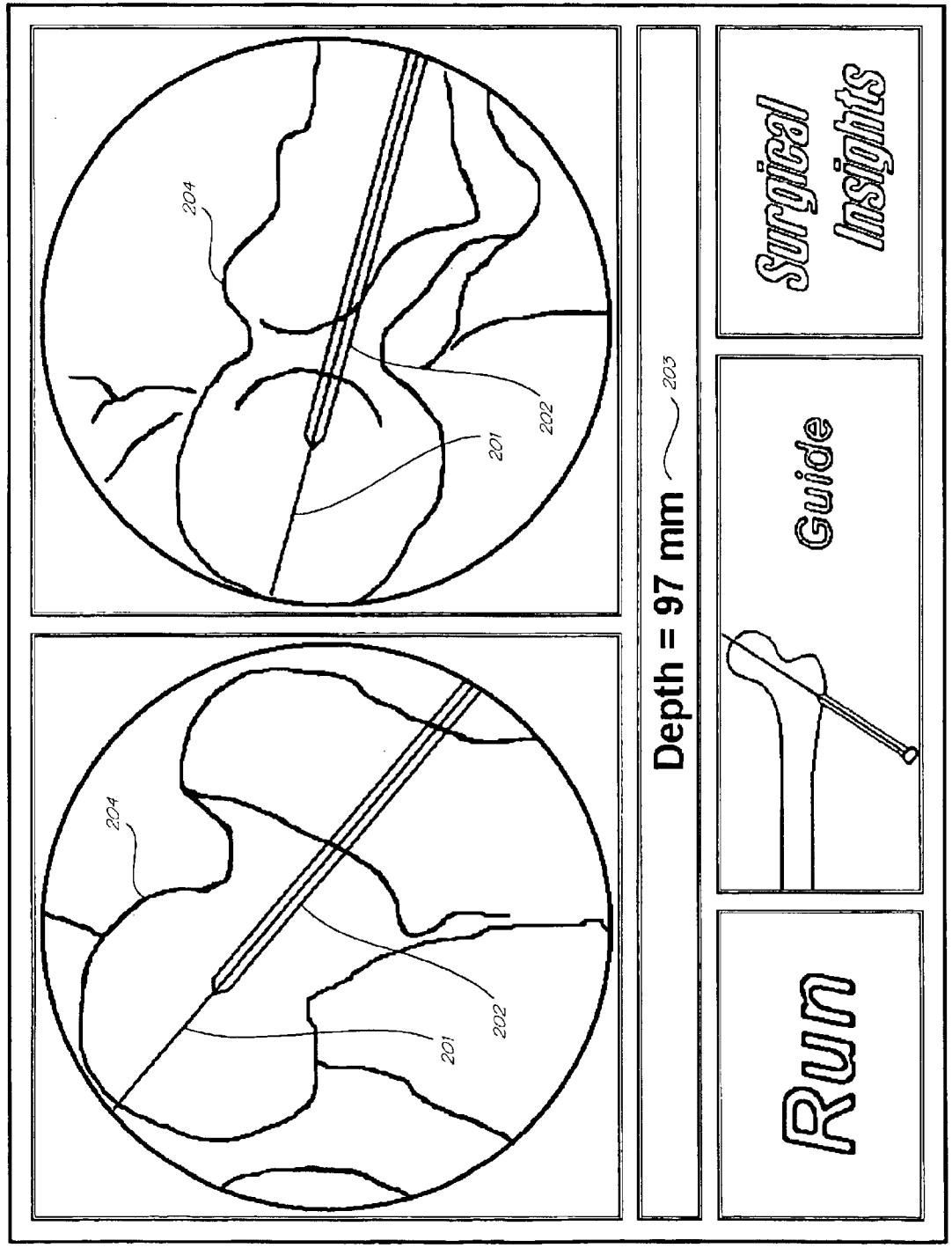
FIG. 4 is an example of a screen display of two images and superimposed instrument representations.

To generate the preferred drill bit representation 202, FIG. 4, the location of the tip 106 of the drill bit 105 must be determined. As seen in FIG. 3, this is preferably accomplished during a calibration step by placing the tip 106 of the drill bit 105 into the dimple 113 on the drill guide 110. The poses of both instruments 100, 110 are recorded when a footswitch is pressed or other triggering means is activated. The location of the tip 106 of the drill bit 105 relative to the drill emitter coordinate frame D can be calculated from the pose of the drill guide 110, the known location of the dimple 113 on the drill guide 110, and the pose of the drill guide coordinate frame, using methods well known in the art. The location $^{D}q$ of the tip 106 of the drill bit 105 with respect to the drill emitter coordinate frame D is then stored in the computer.

In an alternative embodiment, the calibration step is performed by inserting the drill bit 105 into the bore 114 of the drill guide 110 and simultaneously placing the distal end 108 of the drill guide bore 114 and the tip 106 of the drill bit 105 against a rigid object, such as the cortex of a bone. The poses of both instruments 100, 110 are recorded in response to a triggering means, and the location of the tip 106 of the drill bit 105 relative to the drill emitter coordinate frame D is calculated from the pose of the drill guide 110, the known location of the distal end 108 of the bore 114 of the drill guide 110, and the pose of the drill guide coordinate frame, D, using methods well known in the art. The location $^{D}q$ of the tip 106 of the drill bit 105 with respect to the drill emitter coordinate frame D is then stored in the computer.

Alternatively, the tip 106 of the drill bit 105 may be placed in a dimple on an immovable fixture and the drill rotated around this point while positions of the drill's emitters are sampled, as described in U.S. patent application Ser. No. 09/248,133. The tip 106 of the drill bit 105 is defined as the center of the sphere that is described by the drill emitters 101 and is found by numerical methods known in the art. Any other method for determining the position of the drill bit tip may be employed without departing from the instant invention.

Next, in order to display the drill bit 105, its pose must be determined. One suitable pose, $^{O}T_{E}$, represents the pose of the tip 106 of the of the drill bit 105, with respect to the optical localizer when the drill bit 105 is straight. This pose can be calculated using methods well known in the art from the orientation of the drill's axis of rotation relative to the drill emitter coordinate frame D, the pose, $^{O}T_{D}$, of the drill 105 relative to the localizer, and the location $^{D}q$ of the drill bit tip 106 relative to the drill emitter coordinate frame. Turning to FIG. 4, the drill bit's graphic representation 202 can then be calculated from the drill bit pose $^{O}T_{E}$, the drill bit's previously stored 3-D model, and a previously determined model of the C-arm imaging chain. The graphic representation of the drill bit 202 is superimposed on the x-ray images of the body part 204. Alternatively, a 2-D model of the drill bit may be generated and superimposed on the x-ray images based on the tool pose. Additionally, a model of the drill guide may be superimposed on the images using similar techniques.

Figure 5:
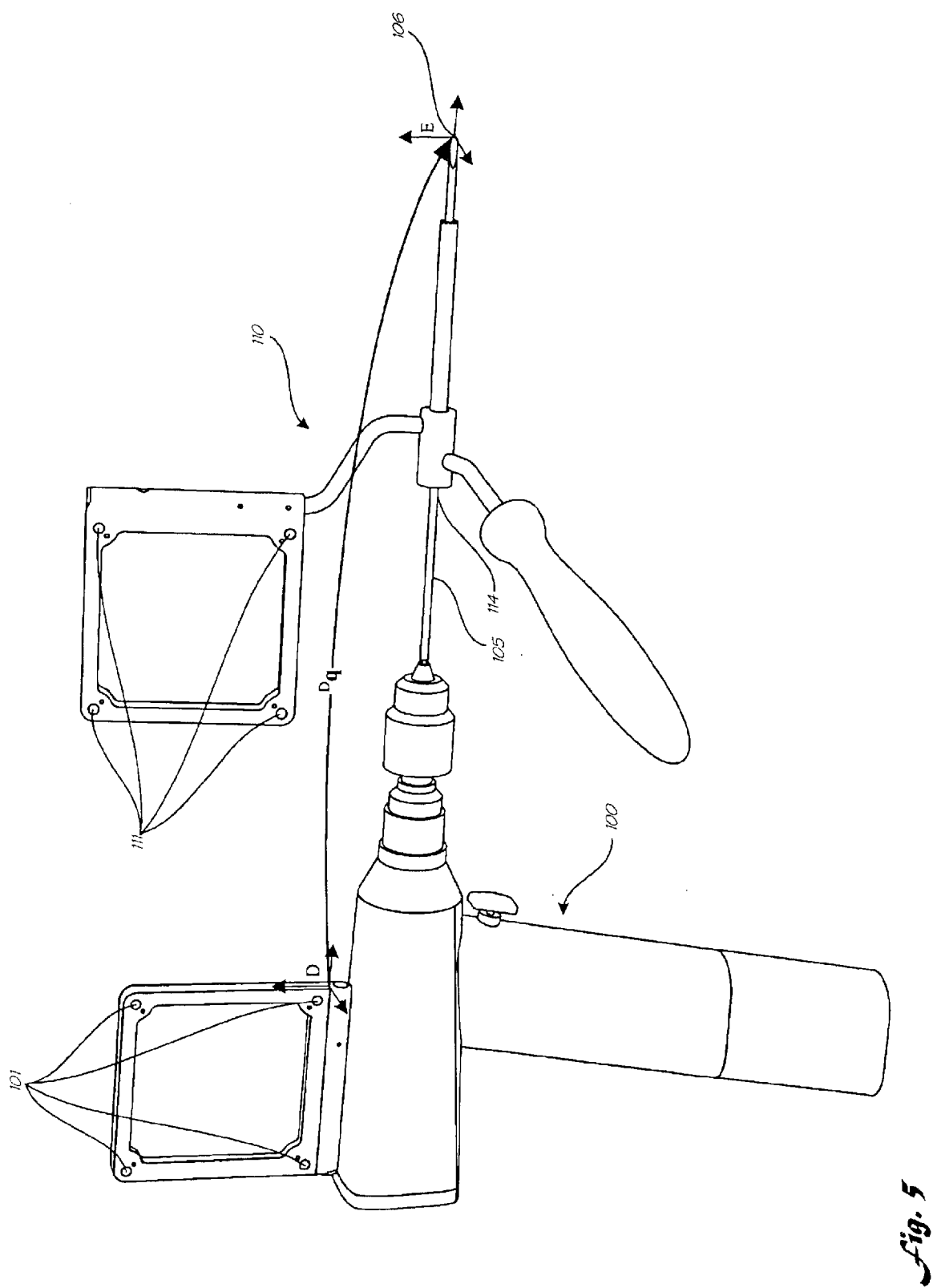
FIG. 5 is a perspective view of the drill and drill guide in position for use in drilling.

For an accurate drill bit representation 202 to be displayed in the foregoing description, the orientation of the drill bit 105 must coincide with the axis of rotation of the drill 100. However, as the drill bit 105 encounters obstacles during insertion into the bone, it may exhibit some flexion relative to the drill 100, causing the actual trajectory at the tip 106 to deviate from the drill bit representation 202. Therefore, in the preferred embodiment shown in FIG. 5, the effects of drill bit flexion are minimized by passing the drill bit 105 through the bore 114 of the drill guide 110 just prior to entry into the body part, significantly reducing the distance over which flexion may occur. In this preferred case, the pose $^{O}T_{E}$ for the tip 106 of the drill bit 105 is calculated more accurately by combining the orientation of the bore 114 of the drill guide 110 with the location of the tip 106 of the drill bit 105. The orientation of the bore 114 of the drill guide 110 is derived from the known orientation of the bore on the drill guide and the pose of the drill guide as measured by the localizing device. The location $^{O}T_{D}$ of the tip 106 of the drill bit 105 is derived from the location $^{D}q$ of the tip 106 relative to the drill emitter coordinate frame D and the pose of the drill as measured by the localizing device.

Additionally, a reference frame can be assigned with an axis parallel to the axis of rotation of the drill 100 and with its origin arbitrarily at the point of attachment of the drill bit to the drill. The orientation and location of this reference frame can be compared with the orientation and location of the bore of the drill guide 114, and the difference reported to the surgeon by means of text or graphics on the display or by an audible alarm or other signal. An error condition can be signaled to the surgeon if the orientations or locations of the two instruments are not sufficiently coincident. For example, a difference in orientation could be caused by excessive flexion of the drill bit 105 or failure to insert the drill bit 105 into the bore 114 of the drill guide 110. A difference in location perpendicular to the axis of rotation of the drill is likely to be caused by failure to insert the drill bit 105 into the bore 114 of the drill guide 110, while a difference along the axis of rotation is normal during drilling and is related to depth of insertion of the drill bit 105.

In general, a plurality of tracked instruments may interact to form more accurate or useful graphic representations by combining or comparing their orientations and locations without departing from the instant invention. In an alternative embodiment, a tracked cutting guide constrains the saw blade of a tracked saw and the graphic representation of the saw blade is generated using the plane defined by the cutting guide, and the position and orientation of the saw.

Figure 6:
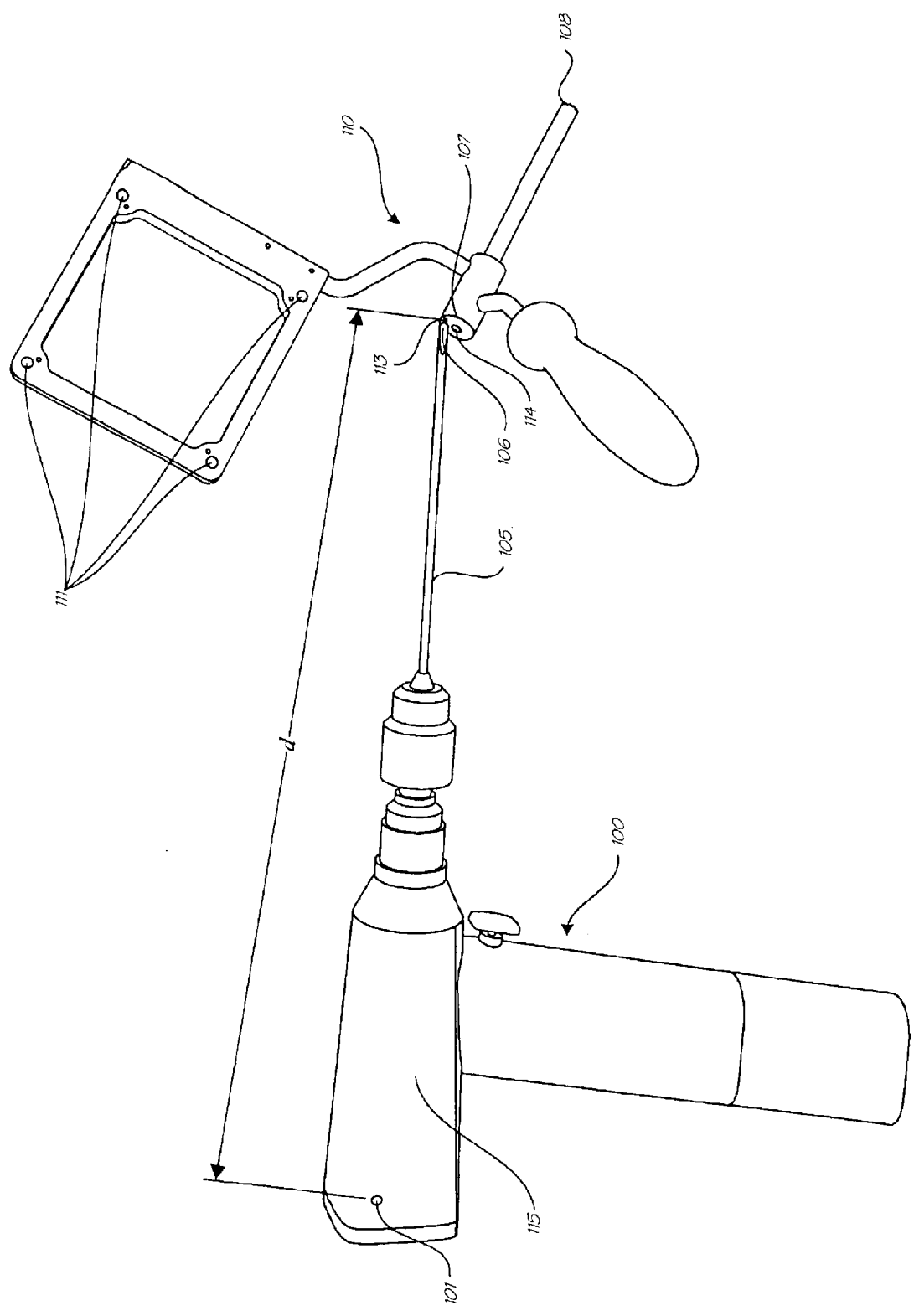
FIG. 6 is a perspective view of a drill with a single localizer emitter integrated into the drill housing and a drill guide in position for calibration.

In an alternative embodiment, shown in FIG. 6, the drill 100 is outfitted with a pair of localizing emitters 101 attached to the drill housing 115. The emitters 101 are attached to either side of the drill housing 115 such that one emitter 101 is viewable by the localizing device during use. Alternatively, the two emitters or reflectors may be mounted on either side of a removable housing that attaches rigidly anywhere on a drill. In another embodiment, a single reflective sphere may be mounted on the top of the drill or on a part of the drill where it is viewable by the localizer from either side of the drill.

In order to generate a graphic representation 202 of the drill bit 105 when only a single emitter 101 is visible on the drill, the distance, d, between the emitter 101 and the tip 106 of the drill bit 105 must be found. This may be calculated during a calibration step as the difference between the position of the drill emitter 101 and a known reference point such as a dimple 113 on the drill guide 110 or the distal end 108 of the bore 114 of the drill guide 110. The surgeon places the tip 106 of the drill bit 105 coincident with the dimple 113 or other reference point and simultaneously presses a footswitch or other triggering device, causing the pose of the drill guide 110 and the location of the drill's emitter 101 to be measured and the difference calculation to be performed.

Figure 7:
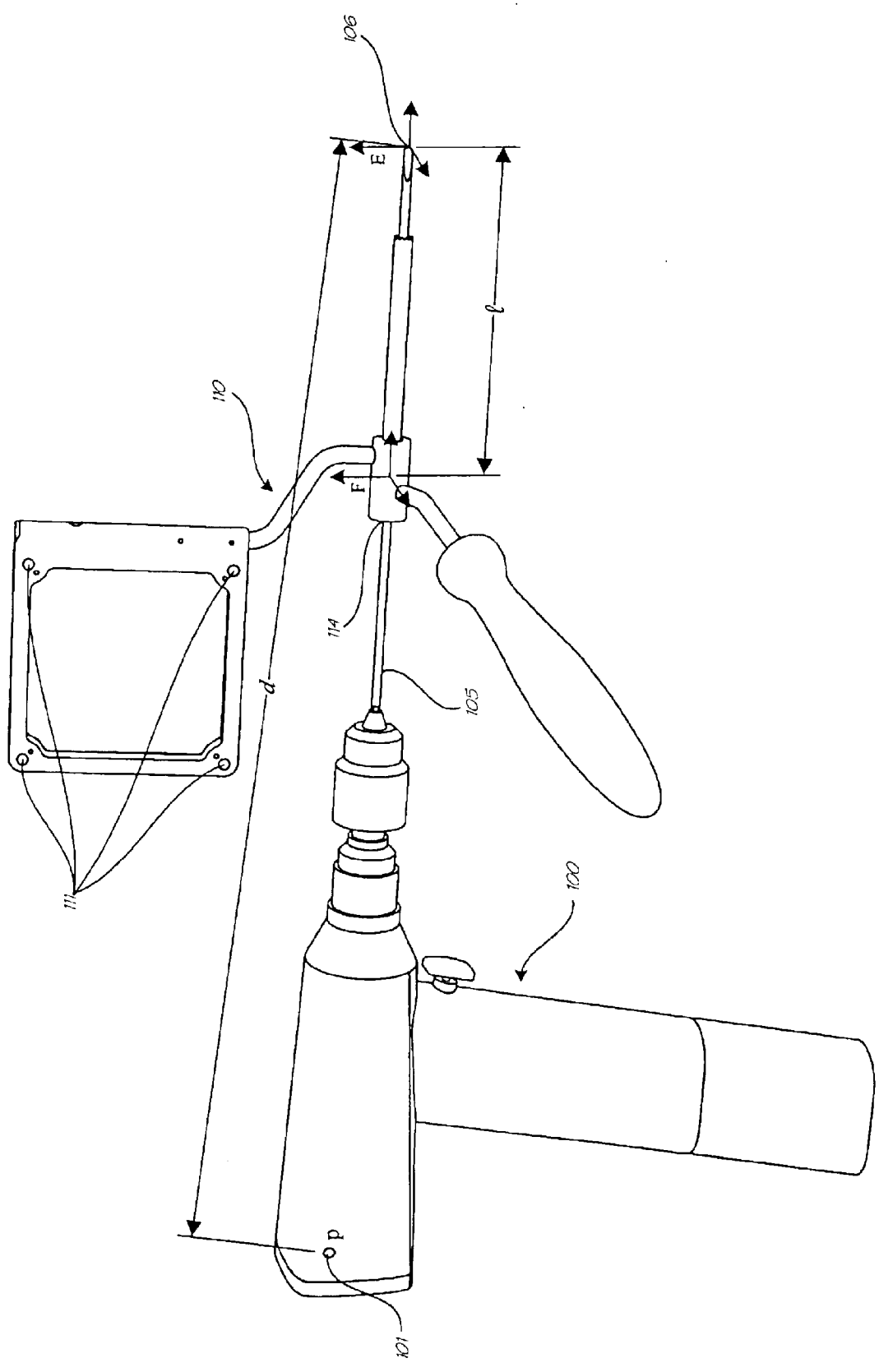
FIG. 7 is a perspective view of the drill of FIG. 6 with an integrated localizer emitter and the drill guide in position for use in drilling.

During drilling, as shown in FIG. 7, while the drill bit 105 is inserted into the bore 114 of the drill guide 110, the pose of the drill guide 110 and the location of the drill's emitter 101 are measured by the localizing device. A coordinate frame F is assigned a position along the bore 114 of the drill guide 110, and its pose $^{O}T_F$ is calculated from the known position of F on the drill guide 110 and from the pose of the drill guide 110 as measured by the localizer. The location $^Fp$ of the drill emitter 101 can then be calculated relative to F. Using this and the stored value of the distance d between the tip 106 of the drill bit 105 and the drill emitter 101, the pose of the tip 106 with respect to the localizer can be calculated by the formula:

$$^{O}T_E = {}^{O}T_F \cdot \begin{bmatrix} 1 & 0 & 0 & 0 \\ 0 & 1 & 0 & 0 \\ 0 & 0 & 1 & l \\ 0 & 0 & 0 & 1 \end{bmatrix}$$

where l is the distance between the tip 106 of the drill bit 105 and the origin of the tool coordinate frame. This is calculated from the equation:

$$l = \sqrt{d^2 - {}^Fp_x{}^2 - {}^Fp_y{}^2} - |{}^Fp_z|$$

where d is the previously determined distance between the drill emitter and tip 106 of the drill bit 105, and $^Fp_x$, $^Fp_y$ and $^Fp_z$ are the Cartesian coordinates of $^Fp$ in coordinate frame F.

Figure 8:
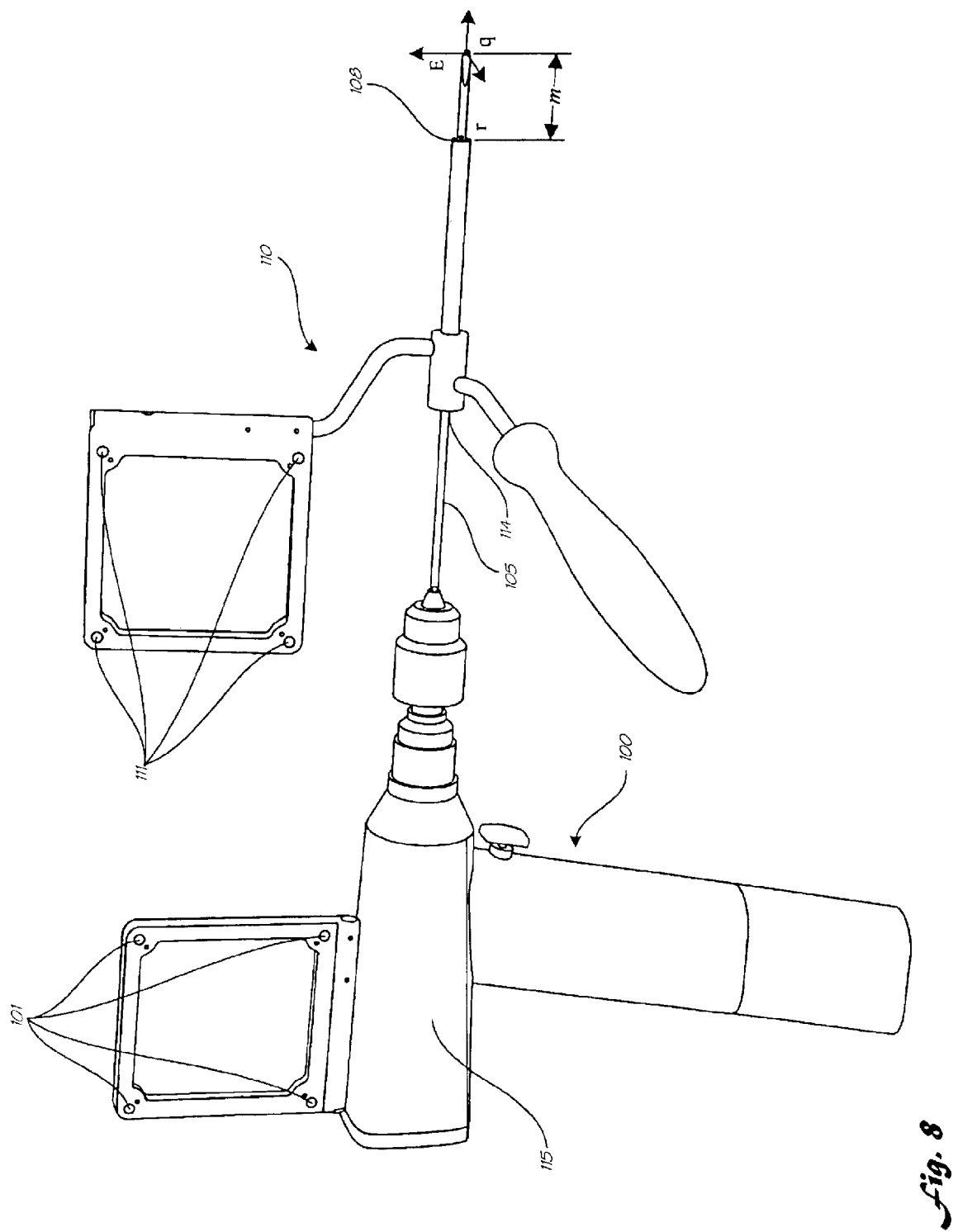
FIG. 8 is a perspective view of the drill and drill guide of FIG. 5 in position for use in drilling.

In the preferred embodiment, shown in FIG. 4, the system begins calculating and displaying the position of the drill bit representation 202 once the footswitch is pressed to perform the calibration step. A second press of the footswitch turns off the calculation and display of the position of the drill bit representation 202. While the drill bit display is active, the system also displays on the monitor a numerical value 203 representing the distance the tip 106 of the drill bit 105 protrudes past a reference point. Preferably, as shown in FIG. 8, the reference point is the distal end 108 of the bore 114 of the drill guide 110. The depth value, m, represents the distance between the drill bit tip 106, at q, and the reference point, at r, on the drill guide 110. The position, $^oq$, of the tip 106 of the drill bit 105 is known from the calculation of the pose $^{O}T_E$ of the drill bit coordinate frame E (for either a single emitter drill or multiple emitter drill). The position, $^or$, of the reference point, is known from the pose of the drill guide 110 as measured by the localizer and the position of point r on the drill guide 110. The depth, m, is calculated as the magnitude of the difference between $^oq$ and $^or$.

Alternatively, the depth may be reported in other formats including a bar graph representation.

The distance traveled by the drill bit 105 may also be calculated and reported for any arbitrary starting and ending points. The starting point may be assigned to be the location of the drill bit tip 106 when the footswitch is pressed a first time and the ending point assigned to be the location when the footswitch is pressed a second time. This can allow, for example, measurement from the lateral cortex to the medial cortex of a bone, regardless of drill guide placement.

Alternatively, the signals to indicate the enabling or disabling of the calculation and display of the drill bit representation, or of the assignment of a starting or ending point for distance calculation, may be generated in any manner without departing from the instant invention. For example, these signals may be generated by the pressing of a trigger on the instrument, the activation of a voice activated switch, or the sensing of the starting or stopping of the drill motor.

Alternatively, a graphic may be employed that displays the representation of the drill bit relative to another surgical instrument or instruments. In this case, the superposition of the instruments on image data is optional and the representation of the drill bit is displayed relative to the representation of another instrument or instruments or relative to the graphics window (where the frame of reference of the graphics window is determined by the pose of the other instrument or instruments).

The herein described invention may be applied to surgeries, surgical instruments and situations beyond those outlined in this description. Other modifications and alternative embodiments of the invention are contemplated which do not depart from the spirit and scope of the invention as defined by the foregoing teachings and appended claims. It is intended that the claims cover all such modifications that fall within their scope.

We claim as our invention:

1. A surgical drill for use with a computer assisted surgery system having a localizing device, the drill having two sides, the drill comprising:

an elongated housing having opposite ends;

a handle attached to the housing and having a bottom area away from the housing; and at least three localizing emitters mounted on and integral with each side of the drill, the emitters on each side arranged such that they are visible to the localizing device when that side is facing the localizing device, the emitters on each side spaced sufficiently apart from one another to provide accurate pose information, wherein, on each side of the drill, two emitters are mounted on opposite ends of the housing.

2. The surgical drill of claim 1, one emitter is mounted on the bottom area of the handle.

3. A surgical drill for use with a computer assisted surgery system having a localizing device, the drill having two sides and opposite longitudinal ends, the drill comprising:

at least three localizing emitters mounted on each side of the drill, the emitter on each side arranged such that they are visible to the localizing device when that side is facing the localizing device, the emitters on each side spaced sufficiently apart from one another to provide accurate pose information, wherein, on each side of the drill, two emitters are mounted on opposite longitudinal ends of the housing.

* * * * *